United States Patent [19]

Heitzmann et al.

[11] Patent Number: 5,171,299
[45] Date of Patent: Dec. 15, 1992

[54] BALLOON CATHETER INFLATION PRESSURE AND DIAMETER DISPLAY APPARATUS AND METHOD

[75] Inventors: Harold A. Heitzmann; Jeffrey S. Dove, both of Irvine; Lauralan T. Grisoni, Aliso Viejo, all of Calif.

[73] Assignee: Baxter International Inc., Deerfield, Ill.

[21] Appl. No.: 739,924

[22] Filed: Aug. 2, 1991

[51] Int. Cl.⁵ ............................................. A61M 29/00
[52] U.S. Cl. ..................................... 604/100; 606/191
[58] Field of Search .................. 606/192, 194; 604/97, 604/96–100, 118; 128/672, 673, 674, 675, 148, DIG. 12, DIG. 13

[56] References Cited

U.S. PATENT DOCUMENTS

| | | | |
|---|---|---|---|
| 5,004,472 | 4/1991 | Wallace | 606/194 |
| 5,009,662 | 4/1991 | Wallace et al. | 606/192 |
| 5,021,046 | 6/1991 | Wallace | 606/97 |

Primary Examiner—C. Fred Rosenbaum
Assistant Examiner—M. Mendez
Attorney, Agent, or Firm—Michael C. Schiffer; Raymond Sun; Debra D. Condino

[57] ABSTRACT

An apparatus for determining fluid pressure and inflation diameter in the balloon of a dilation catheter includes a pressure sensing transducer in fluid communication with the interior of the catheter balloon. The transducer provides a balloon pressure signal which is processed by a microcomputer to determine a balloon diameter or circumference as a function of the balloon pressure. The microcomputer produces a signal representing the balloon diameter or circumference. A digital display responds to the pressure signal and diameter signal to display both balloon pressure and diameter in order to provide an added degree of safety and control to a vascular physician conducting balloon angioplasty or similar procedures.

12 Claims, 2 Drawing Sheets

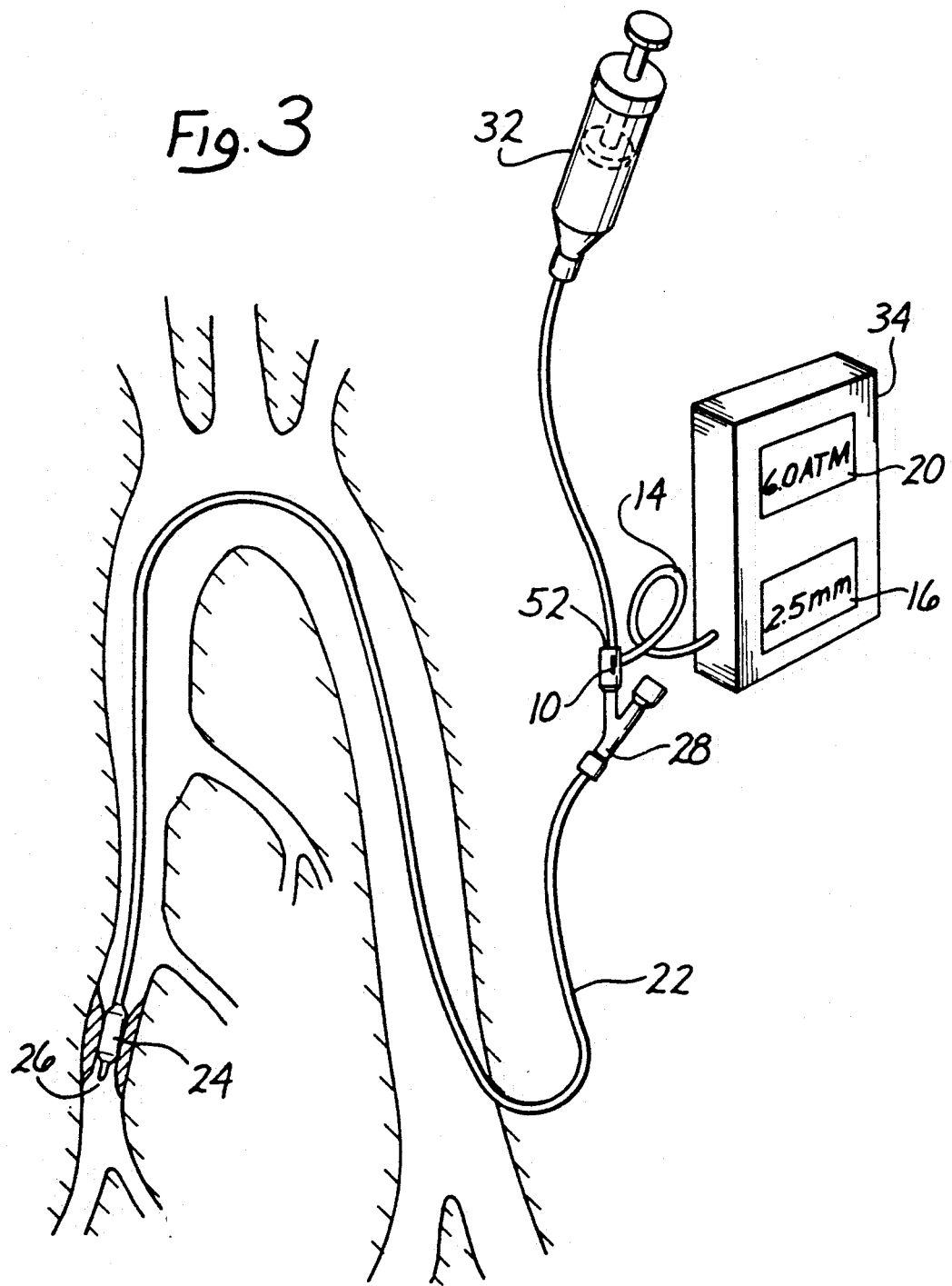

BALLOON CATHETER INFLATION PRESSURE AND DIAMETER DISPLAY APPARATUS AND METHOD

FIELD OF THE INVENTION

The present invention relates in general to the field of dilatation or balloon catheters employed in the treatment of vascular diseases. More particularly, the present invention relates to an apparatus for accurately determining and displaying the inflation pressure and associated diameter or circumference of a balloon catheter during balloon angioplasty and similar medical procedures.

BACKGROUND OF THE INVENTION

A major factor associated with both acute and chronic heart problems is the reduction in blood flow to the heart muscle resulting from restrictions in the coronary blood vessels. In many cases such restrictions are caused by deposits of atherosclerotic plaque deposited on the walls of blood vessels which cause an abnormal narrowing of the lumen or blood vessel channel. When the lumen is sufficiently narrowed that the rate of blood flow restriction becomes critical a variety of medical procedures and techniques are available to the intervening cardiologist in order to restore adequate blood flow. The most common of the currently available medical procedures for treating such stenotic lesions (the abnormal narrowing of a blood vessel due to injury or vascular disease) include pharmacological treatments which dilate the blood vessels, bypass surgery to shunt blood around the lesions, and balloon angioplasty to reopen the narrowed vessels.

Each medical procedure has its own benefits and drawbacks. However, over the last decade balloon angioplasty has become widely accepted as a safe and effective method for treating such vascular diseases in appropriate circumstances. The most common form of angioplasty is called percutaneous transluminal coronary angioplasty or PTCA. Generally, this procedure utilizes a dilatation catheter provided with an inflatable balloon at its distal end. Using a fluoroscope and radiopaque dyes for visualization the interventional cardiologist guides the distal end of the dilation catheter through the vascular lumen into a position across the stenotic lesion. Once positioned the balloon is inflated for a brief duration to displace or otherwise reopen the lesion and reestablish adequate blood flow.

Typically, inflation of the balloon is accomplished by supplying a pressurized fluid through an inflation lumen in the catheter which is connected to an inflation apparatus located outside of the patient's body. Similarly, applying a negative pressure to the inflation lumen collapses the balloon to its minimum dimension for initial placement of the balloon catheter within or removal from the target blood vessel.

A wide variety of angioplasty balloon catheter designs and constructions are available to the vascular physician. Typically, the catheter is constructed of resilient or elastomeric materials configured to produce a specific balloon inflation diameter at a standard inflation pressure of six atmospheres. Because vascular lesions differ in size most balloon catheters are available in stepped dilation diameters ranging from approximately 1.5 millimeter to 4.0 millimeter in 0.5 millimeter or 0.25 millimeter increments. Accordingly, after locating the stenosis in an artery or vessel utilizing a procedure such as an angiogram, a cardiologist is able to guage the size of the lesion and select the appropriately sized balloon to effectively open the lesion.

However, in spite of the high level of training and skill exhibited by today's cardiologists, selecting the appropriately sized balloon catheter is complicated by a variety of factors. In many cases, stenotic lesions exhibit a markedly irregular cross sectional configuration which, when viewed from differing angles, may present deceptively narrow profiles. Additionally, the composition of the stenotic lesion itself may vary from hard, calcified materials to soft, readily displaceable deposits. Because utilization of an inappropriately large balloon may result in undesirable damage to the vascular tissue surrounding the lesion, out of an abundance of caution, balloon size selection generally is biased toward the smallest inflation diameter that will effectively open the stenosis without inducing trauma to the vascular tissue. As a result, when unexpectedly soft or irregularly shaped lesions are encountered what would appear to have been an appropriately sized balloon at first may in fact be undersized and less than effective.

In order to address these problems without the need to replace the initially sized balloon catheter with a larger sized apparatus, many of the current generation of dilation balloons are constructed with a predetermined overinflation diameter which may be as much 20% greater than the standard reference inflation diameter. As a result, the intervening cardiologist may reinflate the balloon catheter to a higher pressure in order to achieve a slightly greater dilation diameter that may effectively open the lesion.

During such initial inflation or reinflation it is desirable for the physician to know the pressure to which the balloon is being inflated in order to insure that the proper diameter has been achieved. At present, inflation pressure usually is displayed by an analog pressure gauge or digital readout which enables the cardiologist to determine that the balloon catheter is being used within its operational pressure range (typically 6 to 12 atmospheres) and below its burst pressure (typically ranging from 10 to 20 atmospheres depending upon balloon construction and materials). Though the current generation of analog pressure gauges are reasonably accurate and easy to read, their accuracy is no better than one half the smallest increment (typically $\frac{1}{8}$ to $\frac{1}{4}$ atmospheres). More importantly, at present there is no convenient way for the cardiologist to determine balloon inflation diameter with any degree of accuracy beyond that expected at the reference inflation pressure of 6 atmospheres. Current technology requires the cardiologist to refer to a graph of balloon inflation diameter versus pressure which is routinely supplied by the catheter manufacturer. Visual interpolation of this graph during angioplasty is difficult at best due to the darkened lighting typically present in the operating room (to assist flouroscopic visualization) and the demanding aspects of the procedure itself.

Accordingly, there is a need for an apparatus and method that will effectively communicate real time inflation balloon diameters and pressures to a vascular physician during a balloon dilation procedure. Additionally, there is a need to enable a vascular physician to accurately manipulate the effective diameter of an inflation balloon over as wide a range of dimensions and pressures as possible while remaining below the balloon burst pressure. Such an apparatus should be simple and easy to use, relatively inexpensive, and capable of interfacing with existing operating room monitors and displays if desired.

SUMMARY OF THE INVENTION

These and other objects are achieved by the apparatus of the present invention which, in accordance with broad structural aspects thereof, includes a pressure sensor and means for determining balloon diameter of circumference as a function of fluid pressure and means for displaying this information to the vascular physician. Preferably, the pressure sensor includes an element for providing an electrical signal which is a function of the pressure in the interior of the balloon or inflation lumen. Balloon diameter or circumference is determined from this signal utilizing the characteristic compliance curves of the inflation balloons and both the fluid pressure and balloon inflation diameter or circumference are displayed in a manner that can be readily discerned by the vascular physician utilizing the apparatus.

In a broad aspect, the apparatus of the present invention enables the vascular physician to determine both fluid pressure and inflation diameter or circumference in a balloon catheter by sensing the fluid pressure in the balloon and providing a pressure signal, determining the resultant balloon diameter or circumference, and producing a representative signal for display of the balloon diameter or circumference and fluid pressure. In this manner, the vascular physician is able to accurately control balloon diameter while maintaining the balloon pressure below the specific balloon burst pressure.

In alternative embodiments of the present invention, the apparatus may be provided with its own, self-contained digital or auditory display or the output signal may be interfaced with existing operating room display monitors. In one exemplary embodiment of the present invention, the display data of balloon pressure and inflation diameter or circumference is provided in conjunction with the X ray or fluoroscopic images of the vascular lesion being treated to provide the vascular physician with the physical data regarding balloon operation in direct conjunction with the visual aspects of the procedure.

Further adding to the advantages of the present invention, the individual components or element of the apparatus are readily available from commercial sources in bulk quantities. Thus, the apparatus of the present invention is simple and inexpensive to operate and produce. Moreover, the apparatus is compact, easily sterilizable or packaged in sterile configuration and incorporated can be simply into existing angioplasty procedures.

Additional features and advantages of the present invention will become apparent to those skilled in the art from the following detailed description of exemplary embodiments thereof, taken in conjunction with the accompanying drawings which illustrate, by way of example, the principles of the present invention.

BRIEF DESCRIPTION OF THE DRAWINGS

FIG. 3 is an elevational view illustrating an embodiment of the present invention used in conjunction with a conventional dilation balloon catheter.

DETAILED DESCRIPTION

Figure 1:
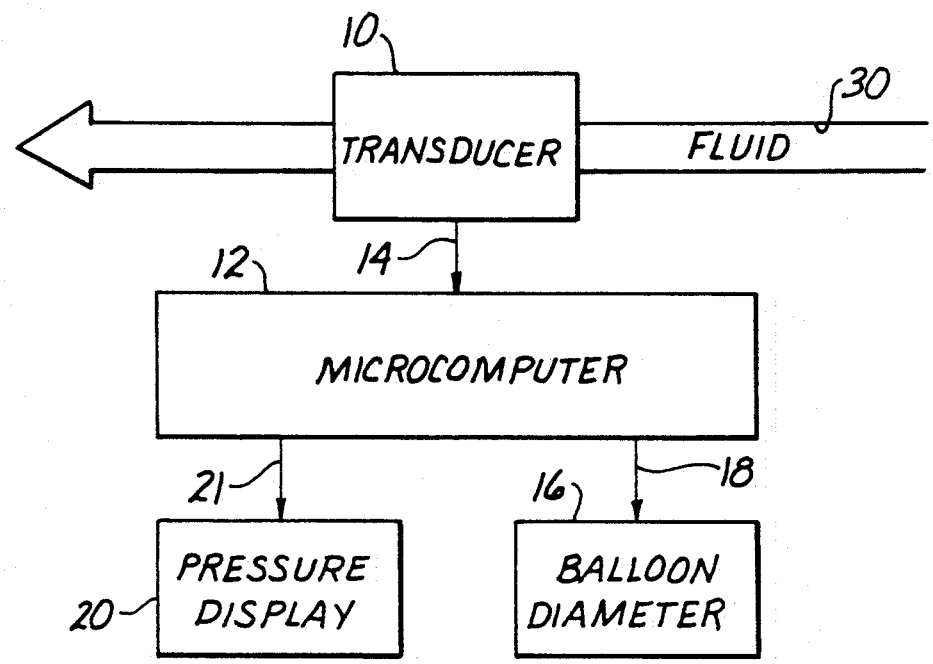
FIG. 1 is a schematic representation of an exemplary embodiment of the present invention.

Referring more particularly to the drawings in which similar reference numerals indicate similar parts throughout the several views of the drawings, FIG. 1 shows a schematic diagram of the basic elements comprising the apparatus of the present invention. Pressure sensing transducer 10 is in fluid sensing communication with the fluid conducting lumen 30 of a balloon catheter (not shown in FIG. 1). Pressure sensing transducer 10 senses the fluid pressure within lumen 30 and provides a pressure signal in response thereto. Preferably, pressure sensing transducer 10 utilizes a piezoelectric diaphragm or crystal to generate an electrical signal corresponding to the fluid pressure monitored by transducer 10 These pressure signals are transmitted to microcomputer 12 as represented by cable 14. Utilizing the fluid pressure signal from transducer 10 microcomputer 12 determines the corresponding balloon diameter or circumference and produces a corresponding signal representing this balloon diameter or circumference. This signal is transmitted to balloon display 16 as represented by line 18. Concurrently with this function, microcomputer 12 also produces a corresponding signal representing the fluid pressure which is transmitted to pressure display 20 as represented by line 21. In this manner, the fluid pressure within lumen 30 is utilized to produce an accurate, simultaneous, real time display of inflation balloon diameter or circumference as a function of the correspondingly displayed fluid pressure. Thus, as pressure is varied by the vascular physician the corresponding dimensions of the inflated balloon also will vary and be reflected in the appropriate display.

As those skilled in the art will appreciate, while inflation balloons generally are standardized to specific inflation diameters at set pressures, it is not uncommon for the balloon to assume a less than circular cross sectional configuration when inflated across an irregularly shaped stenotic lesion. Accordingly, it may be desirable to display the calculated balloon circumference as opposed to the balloon diameter. Regardless of the dimensional perimeter utilized, the present invention is not limited to either diameter or circumference as it is the concept of displaying an appropriate dimensional characteristic as a function of inflation pressure that is more fundamental to the apparatus and process of the present invention.

Similarly, as those skilled in the art will appreciate, calculated balloon diameters are only accurate after the balloon is unfolded fully inside the vessel. Generally, this point is determined by the physician who visually recognizes the appropriate cylindrical shape of the balloon in the fluoroscope. This condition also applies to the current practice of estimating balloon diameters by referring to the appropriate compliance curves supplied with the device.

Pressure sensing transducer 10 may be any of the commercially available pressure sensing devices such as the piezoelectric transducer disclosed in U.S. Pat. No. 4,610,256. Alternatively, appropriately calibrated transducers (engineered to measure pressures ranging from approximately 1 to 20 atmospheres) may be obtained from Motorola and other commercial manufacturers and utilized in accordance with the teachings of the present invention.

Generally speaking, as known in the art the apparatus of the present invention will provide an electrical voltage to transducer 10 (for example, 5 V) which is modulated by transducer 10 in response to the inflation pressure in lumen 30. The output voltage of transducer 10 (for example, approximately 5 mV per atmosphere) is returned to microcomputer 12 for further processing. Regardless of the type or source of pressure sensing transducer utilized, the operative fact is that fluid pressure is sensed and a balloon pressure signal is provided to microcomputer 12.

Microcomputer 12 preferably includes all of the necessary interface circuitry for receiving input and control signals and for transmitting display signals to balloon display 16 and pressure display 20. If desired, microcomputer 12 also may include a buffer/amplifier to condition the balloon pressure signal received from transducer 10 as well as functions for filtering, temperature compensation and the like, as known in the art. It will also be appreciated by those skilled in the art that discrete electrical components may be utilized to control the functioning of the apparatus of the present invention in place of microcomputer 12. However, microcomputer 12 is preferred for reasons of simplicity and packaging.

Balloon display 16 and pressure display 20 preferably are electronic digital displays of conventional construction such as liquid crystal, LED, or electroluminescent displays. Preferably, balloon display 16 will display balloon diameter in large, easy to read characters calibrated in fractions of a millimeter or other suitable unit of measure. Similarly, pressure display 20 preferably will display fluid pressure in large, easily read characters calibrated in tenths of hundredths of an atmosphere, pounds per square inch or other suitable unit of pressure. At present, atmospheres are the preferred units of measure as currently available dilation balloon catheters are dimensionally calibrated at whole unit atmospheric pressures. Thus, providing fractional pressure readouts in increments of 0.1 to 0.01 atmospheres provides a vascular physician with an unprecedented degree of pressure control.

Figure 2:
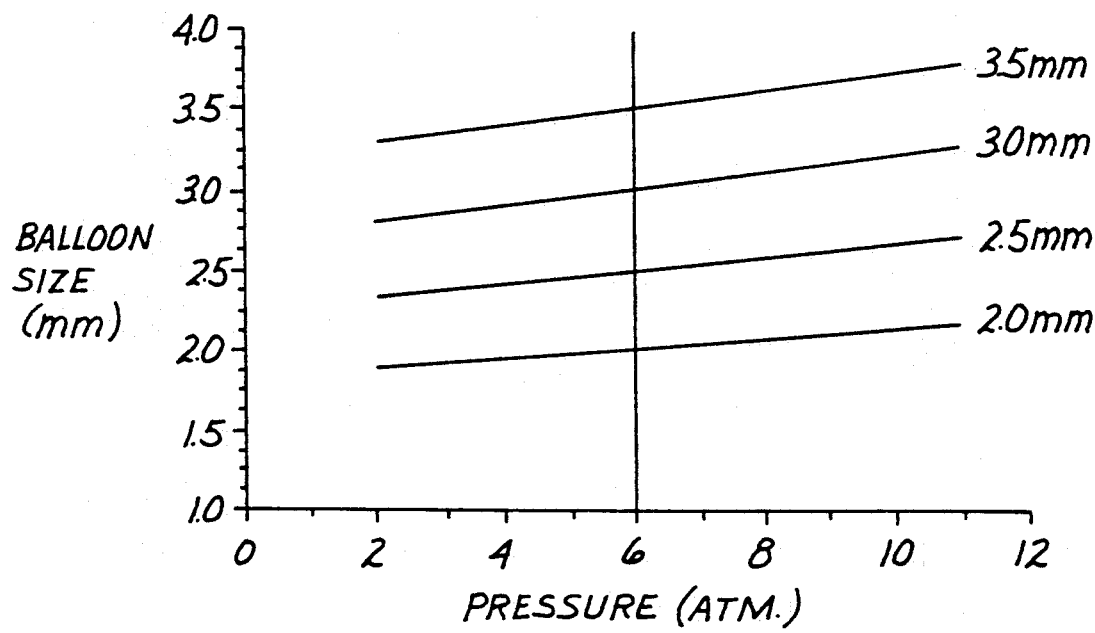
FIG. 2 is an exemplary balloon compliance curve illustrating representative balloon sizes as a function of pressure for use in accordance with the teachings of the present invention.

Microcomputer 12 also includes means for determining balloon diameter or circumference as a function of fluid pressure. Preferably, this means for determining balloon diameter or circumference is a look-up table stored in the memory of microcomputer 12 incorporating the features of one or more representative balloon compliance curves as represented in FIG. 2. As shown in FIG. 2, the diameter of an inflation balloon will vary as a function of pressure. In the exemplary, balloon compliance curve of FIG. 2 four reference balloons are standardized at specific diameters ranging from 2.0 millimeters to 3.5 millimeters at 6 atmospheres of pressure. Because of the material properties of the various polymers and elastomers forming these exemplary and most typical balloon catheters, varying the balloon inflation pressure, for example, from 2 to 12 atmospheres will change the inflated balloon diameters by several tenths of a millimeter above or below the standard reference diameter. The rate of diameter change is relatively constant and increases from low pressure to high pressure along a generally smooth positive slope with the greatest slopes appearing in the largest diameter standard sized balloons.

It is contemplated as being within the scope of the present invention to code in different balloon dimensions or compliance curves into microcomputer 12 as necessary corresponding to different balloon characteristics. Similarly, where different size balloons are utilized it may be necessary to input the standard reference balloon diameter into microcomputer 12 such that microcomputer 12 can select the appropriate compliance curve from its memory to determine the appropriate balloon diameter or circumference as a function of fluid pressure sensed at transducer 10. Along these lines, it is also contemplated as being within the scope of the present invention to provide microcomputer 12 with the capacity to receive such input in any suitably convenient manner such as through switches or keys (not shown) as known in the art.

Turning to FIG. 3, an exemplary embodiment of the present invention is shown in use during a coronary angioplasty procedure in conjunction with a conventional balloon catheter. Dilation catheter 22 is provided with an inflatable balloon 24 at its distal end 26. Y-fitting 28 connects fluid conducting lumen 30 (not shown in FIG. 3) to an inflation/deflation syringe 32 to provide a fluid path between the interior of balloon 24 and the external source of balloon inflating fluid, the inflation/deflation syringe 32.

Pressure sensing transducer 10 is disposed within housing 52 in fluid conducting communication with lumen 30. As those skilled in the art will appreciate, in the present invention housing 52 replaces the prior art analog pressure gauges utilized to monitor balloon pressure. Additionally, it should be emphasized that pressure sensing transducer 10 is illustrated within housing 52 as exemplary of the present invention only. As long as transducer 10 is in fluid conducting communication with the interior of inflation balloon 24, the function of the present invention can be achieved. Accordingly, transducer 10 can be located in any convenient position within the apparatus and may be connected directly to the source of balloon inflation fluid or anywhere further downstream that would not interfere with the angioplasty function of the apparatus.

Cable 14 connects pressure sensing transducer 10 to casing 34. It should be emphasized that cable 14 is exemplary only and that transducer 10 may be integrated into casing 34 such that the integrated unit resides as a part of or attached to dilation catheter 22.

Casing 34 contains the majority of the electronics of the present invention. More particularly, casing 34 holds microcomputer 12 (FIG. 1) and the interface circuitry between balloon display 16 and pressure display 20. Casing 34 may be hand held or pole mounted as desired.

Alternatively, it is also contemplated as being within the scope of the present invention to incorporate balloon display 16 and pressure display 20 within existing operating room monitors This can be accomplished through a simple electrical interface or telemetry as is known in the art. In this manner, it is possible to display the balloon pressure and inflation diameter in conjunction with additional information already present on the operating room monitor (not shown).

Because the apparatus of the present invention provides a vascular physician with the ability to determine both fluid pressure and balloon inflation diameter during angioplasty or similar vascular procedure, it results in a safer medical procedure. The physician is provided with an added degree of control over the inflation diameter plus a significantly enhanced safety margin. This latter benefit is accomplished by providing the vascular physician with the ability to clearly know the balloon inflation pressure relative to the balloon failure point. Thus, where necessary, the vascular physician is able to achieve maximal balloon dilation without fear of balloon failure. Additionally, the ability to accurately control balloon dilation may provide the vascular physician with the ability to open a troublesome vascular lesion without having to retract and replace the inflation balloon with a large diameter balloon catheter.

In closing it is to be understood that the embodiments of the present invention disclosed herein are illustrative of the principles of the invention and that other modifications may be employed which are within the scope thereof. Thus, by way of example, but not of limitation, alternative transducers may be utilized in place of the exemplary piezoelectric transducer disclosed. Similarly, the location of the transducer may be modified as desired and alternative forms of electronic circuitry may be utilized to determine balloon diameter as a function of balloon inflation pressure. Accordingly, the present invention is not limited to that precisely as shown and described in the specification.

What is claimed:

1. An apparatus for determining fluid pressure and inflation diameter or circumference in a balloon catheter, said apparatus comprising:
   a pressure sensor for sensing fluid pressure in said balloon and providing a balloon pressure signal;
   means for determining a balloon diameter or circumference when fluid has been injected into said balloon; and
   means for producing a signal representing said balloon diameter or circumference for display of said fluid pressure and said balloon diameter or circumference; said means for determining a balloon diameter or circumference is a microcomputer provided with at least one balloon compliance curve.

2. The apparatus of claim 1 wherein said pressure sensor is a piezoelectric transducer.

3. The apparatus of claim 1 wherein said means for determining a balloon diameter or circumference is a look-up table stored in a memory of said microcomputer and incorporating data corresponding to said at least one balloon compliance curve.

4. The apparatus of claim 1 wherein said microcomputer is provided with means for inputting at least one dilation balloon standardized diameter.

5. The apparatus of claim further comprising means for converting said signal for display into a visual image.

6. An apparatus for determining fluid pressure and inflation diameter or circumference in the balloon of a dilation catheter, said apparatus comprising:
   means for sensing fluid pressure within said balloon and providing a balloon pressure signal;
   means for determining a balloon diameter or circumference as a function of said balloon pressure signal;
   means for producing a balloon diameter or circumference signal;
   means for displaying said balloon pressure signal and said balloon diameter or circumference signal; said means for determining a balloon diameter or circumference as a function of said balloon pressure signal is a microcomputer; and said microcomputer is provided with a memory incorporating data corresponding to at least one balloon compliance curve.

7. The apparatus of claim 6 wherein said means for sensing fluid pressure is a piezoelectric transducer.

8. The apparatus of claim 6 wherein said means for displaying said balloon pressure signal and said balloon diameter or circumference signal is a digital readout.

9. The apparatus of claim 8 wherein said digital readout is a liquid crystal.

10. The apparatus of claim 8 wherein said digital readout is a light emitting diode.

11. The apparatus of claim 8 wherein said digital readout is an electroluminescent panel.

12. A method for determining fluid pressure and inflation diameter or circumference in the dilation balloon of a balloon catheter, said method comprising the steps of:
   sensing fluid pressure in said balloon and providing a balloon pressure signal;
   determining a balloon diameter or circumference as a function of said balloon pressure signal by a microcomputer provided with a memory incorporating data corresponding to at least one balloon compliance curve;
   producing a signal representing said balloon diameter or circumference; and
   displaying said balloon pressure signal and said signal representing said balloon diameter or circumference.

* * * * *